US012260731B2

(12) United States Patent
Netscher et al.

(10) Patent No.: US 12,260,731 B2
(45) Date of Patent: *Mar. 25, 2025

(54) SYSTEM AND METHOD FOR DETECTING, RECORDING AND COMMUNICATING EVENTS IN THE CARE AND TREATMENT OF COGNITIVELY IMPAIRED PERSONS

(71) Applicant: SafelyYou Inc., San Francisco, CA (US)

(72) Inventors: George Netscher, Berkeley, CA (US); Julien Jacquemot, Berkeley, CA (US); Pulkit Agrawal, Berkeley, CA (US); Alexandre Bayen, Piedmont, CA (US)

(73) Assignee: Safely You Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/400,622

(22) Filed: Dec. 29, 2023

(65) Prior Publication Data

US 2024/0135796 A1 Apr. 25, 2024

Related U.S. Application Data

(63) Continuation of application No. 17/556,372, filed on Dec. 20, 2021, now Pat. No. 11,900,782, which is a (Continued)

(51) Int. Cl.
*G08B 21/04* (2006.01)
*G06F 40/169* (2020.01)
(Continued)

(52) U.S. Cl.
CPC ....... *G08B 21/0476* (2013.01); *G06F 40/169* (2020.01); *G06N 3/08* (2013.01);
(Continued)

(58) Field of Classification Search
None
See application file for complete search history.

(56) References Cited

U.S. PATENT DOCUMENTS 6,263,088 B1 7/2001 Crabtree et al.
6,424,370 B1 * 7/2002 Courtney .................. G06T 7/20
348/135

(Continued)

OTHER PUBLICATIONS

International Search Report and Written Opinion issued in PCT/US19/22306, dated Jul. 11, 2019, 6 pages.

*Primary Examiner* — Fekadeselassie Girma
(74) *Attorney, Agent, or Firm* — COOLEY LLP

(57) ABSTRACT

A system and method for detecting, recording and communicating events involved in the care and treatment of cognitively impaired persons through detection, video recording, storage and communication. The system includes video cameras that typically begin recording upon detecting motion, a local computing unit at the care location that detects alerts, and a cloud or other remote computing and transmission unit. The local computing unit aggregates, stores, processes, and transmits data including performing event detection through an artificial intelligence technique and generating appropriate alerts. The cloud computing aggregates data from many managed care communities, trains new convolutional neural networks from this data, distributes these networks to the local computing units to perform event detection, and provides a platform for various stakeholders to view the collected video data and generated alerts.

22 Claims, 4 Drawing Sheets

Related U.S. Application Data continuation of application No. 15/920,534, filed on Mar. 14, 2018, now Pat. No. 11,232,694.

(51) Int. Cl.
  *G06N 3/08* (2023.01)
  *G06V 20/40* (2022.01)
  *G06V 20/52* (2022.01)
  *G16H 40/20* (2018.01)

(52) U.S. Cl.
  CPC .............. *G06V 20/41* (2022.01); *G06V 20/52* (2022.01); *G08B 21/043* (2013.01); *G16H 40/20* (2018.01)

(56) References Cited

U.S. PATENT DOCUMENTS

| | | |
|---|---|---|
| 6,965,694 B2 | 11/2005 | Ueda et al. |
| 11,232,694 B2 * | 1/2022 | Netscher ............... G06F 40/169 |
| 11,900,782 B2 * | 2/2024 | Netscher ............... G06V 20/52 |
| 2001/0029578 A1 | 10/2001 | Delchini |
| 2002/0077124 A1 | 6/2002 | Hunzinger |
| 2003/0058111 A1 | 3/2003 | Lee et al. |
| 2007/0162304 A1 | 7/2007 | Rodgers |
| 2008/0001735 A1 * | 1/2008 | Tran ......................... A43B 3/48 340/539.22 |
| 2011/0103646 A1 * | 5/2011 | Zeller ................... G06Q 30/02 382/103 |
| 2012/0127306 A1 * | 5/2012 | Oh ....................... G06V 40/113 348/143 |
| 2012/0314901 A1 * | 12/2012 | Hanson .................. G16H 40/67 600/595 |
| 2014/0085501 A1 | 3/2014 | Tran |
| 2014/0241695 A1 * | 8/2014 | Mohan ............... G08B 13/1968 386/234 |
| 2016/0042621 A1 | 2/2016 | Hogg et al. |
| 2016/0364617 A1 * | 12/2016 | Silberschatz ........ G06V 40/103 |
| 2017/0337469 A1 * | 11/2017 | Debes .................... G06N 3/049 |
| 2018/0012463 A1 * | 1/2018 | Chaudhry ............... G06T 7/246 |
| 2018/0113577 A1 * | 4/2018 | Burns .................... G06F 16/739 |
| 2018/0115788 A1 * | 4/2018 | Burns .................... G06V 20/52 |
| 2018/0232592 A1 * | 8/2018 | Stewart ............ G08B 13/19606 |
| 2018/0349708 A1 * | 12/2018 | van Hoof ......... G08B 13/19684 |
| 2018/0357870 A1 * | 12/2018 | Siminoff .......... G08B 13/19608 |
| 2019/0034716 A1 * | 1/2019 | Kamarol ............... G06V 10/764 |
| 2019/0141298 A1 | 5/2019 | Vaidya et al. |
| 2020/0051596 A1 | 2/2020 | Bose et al. |

* cited by examiner

SYSTEM AND METHOD FOR DETECTING, RECORDING AND COMMUNICATING EVENTS IN THE CARE AND TREATMENT OF COGNITIVELY IMPAIRED PERSONS

CROSS-REFERENCE PARAGRAPH

This application is a continuation of U.S. patent application Ser. No. 17/556,372, filed Dec. 20, 2021, and entitled "System and Method for Detecting, Recording, and Communicating Events in the Care and Treatment of Cognitively Impaired Persons," now U.S. Pat. No. 11,900,782, which is a continuation of U.S. patent application Ser. No. 15/920,534, filed Mar. 14, 2018, and entitled "System and Method for Detecting, Recording, and Communicating Events in the Care and Treatment of Cognitively Impaired Persons," now U.S. Pat. No. 11,232,694, the disclosure of each of which are incorporated herein by reference in their entirety.

BACKGROUND

Field of the Invention

The present invention relates generally to the field of video monitoring and more particularly to a method and apparatus for activity recognition such as detecting and preventing rare events like falls, wandering and patient movements in the care of cognitively impaired persons.

Description of the Problem and Prior Art

The problem solved is monitoring cognitively impaired persons in care facilities or elsewhere that suffer from dementia or other mental impairments caused by Alzheimers Disease, Parkinson's Disease, head injuries and other memory or motor function deficiencies. Primary dangers to these persons include the danger of a fall, wandering and development of bed sores (also known as pressure ulcers) caused by non-movement. It is practically impossible at patient care facilities for humans to monitor all patients all of the time. Therefore, falls occur quite regularly causing numerous injuries, some very serious. Unsupervised wandering creates an additional patient safety issue. Patients who do not move, or do not receive attention for periodic movement, are susceptible to increased medical conditions such as bed sores. It would be extremely advantageous to be able to monitor such patients using video cameras with a system that can detect, record and notify caretakers when the person falls, wanders or is not attended to regularly. It would also be very advantageous to have recorded video data of falls or other events that has been annotated by an occupational therapist or other qualified technical person. This annotated data would help a facility to not only detect falls and events when they occur, but also provide information on the nature of injury and also prevent future falls by analyzing causes.

Dementia and other cognitive impairment conditions are a massive and growing problem with limited solutions to mitigate the issues they pose. Current dementia care methods for handling high risk require assigning an at-risk individual to a staff member, referred to as a one-to-one, to be with them at all times. However, as stated above, this becomes impractical and very expensive if there are multiple such patients in a facility. The same care methods are applied for support of individuals with traumatic brain injury, delirium, and various other cognitive impairments. Technology approaches such as bed alarms, wearable pendants, and non-wearable solutions such as radar and optical sensors have only addressed detecting a significant event and do not allow users to observe how issues causing such events occur or the nature of the injury received. Increased medical costs are the result of patient inability to communicate the cause and nature of their injury, resulting in needless and expensive testing for diagnosis and treatment.

Event detection methods based on video have been developed and actively researched, but have not been incorporated into a method and apparatus for detecting and preventing events in for the cognitively impaired. SAR (Synthetic Aperture Radar) is one method that has been used to detect moving objects or people. Force-sensitive floor mats which track people based on their footsteps is another method being tested. However, this technology is quite invasive and costly, and furthermore is not yet capable of robustly handling false alarms. Traditional approaches include wearable pendants to detect falls such as the Philips Lifeline and pressure sensitive bed alarms which detect when an at-risk individual rises from bed without help. Many other approaches have been developed for detecting falls, wandering, and other acute events, but none of these specifically address how the event occurred by collecting video of the event and using this video for event detection. Finally, vision-based solutions for multi-person tracking and event detection have been developed, but none address developing a screening tool for high-risk event detection and prevention in care for the cognitively impaired.

Applications of video based methods have been applied to support elder care for specific uses such as falls. There is no existing system for detecting and preventing adverse events in care for the cognitively impaired solely through the application of artificial intelligence methods to a real-time video stream. Current methods are application specific such as detection methods for detecting falls only. No method using video recording alone, or video alongside other sensors, is available for general detection, analysis, treatment and prevention of adverse events for the cognitively impaired.

Lee in U.S. published patent application number 2003/0058111 discloses a computer vision-based elder-care monitoring system. This system tracks a person of interest in a home setting. Ueda in U.S. Pat. No. 6,965,694 teaches a motion information recognition system using eigenvectors and inner products. Dolkor in US published patent application number 2001/0029578 teaches gesture recognition using image clustering. Crabtree in U.S. Pat. No. 6,263,088 discloses a system and method for tracking movement of objects in a scene. None of these references teach or suggest using an artificial intelligence technique such as a neural network to detect and prevent falls suffered by impaired individuals.

Neural networks, and particularly convolutional neural networks are known in the art.[1] Convolutional Neural Networks are very similar to ordinary Neural Networks. They are made up of neurons that have learnable weights and biases. Each neuron receives some inputs, performs a dot product and optionally follows it with a non-linearity. The whole network still expresses a single differentiable score function: from the raw image pixels on one end to class scores at the other. Convolutional neural net architectures make the explicit assumption that the inputs are images, which allows encoding of certain image properties into the architecture. These then make the forward function more efficient to implement and vastly reduce the amount of parameters in the network. Regular neural networks receive an input (a single vector), and transform it through a series of hidden layers. Each hidden layer is made up of a set of neurons, where each neuron is fully connected to all neurons in the previous layer, and where neurons in a single layer function completely independently and do not share any connections. The last fully-connected layer is called the "output layer" and in classification settings, it represents the class scores. It is known that regular neural nets do not scale well to full images because of the very large number of connections and related parameters.

[1] Description of convolutional neural networks paraphrased from notes for CS-231 at Stanford University.

Convolutional Neural Networks, on the other hand, take advantage of the fact that the input consists of images, and they constrain the architecture in a more sensible way. In particular, unlike a regular Neural Network, the layers of a convolutional neural net typically have neurons arranged in three dimensions: width, height, depth. For example, the input images represent an input volume of activations, and the volume has dimensions of width, height, depth respectively. The neurons in a layer are typically only connected to a small region of the layer before it instead of all of the neurons in a fully-connected manner. Moreover, the final output layer has much smaller dimension numbers because, by the end of the chain, the architecture typically reduces the full image into a single vector of class scores arranged along the depth dimension.

The convolutional neural network layer's parameters consist of a set of learnable filters. Every filter is small spatially (along width and height), but extends through the full depth of the input volume. During the forward pass, the system convolves each filter across the width and height of the input volume, and computes dot products between the entries of the filter and the input at any position. This produces a 2-dimensional activation map that gives the responses of that filter at every spatial position. The network can be made to learn various filters that activate when they see some type of visual feature such as an edge or some orientation or a blotch of some color on the first layer, or eventually entire honeycomb or wheel-like patterns on higher layers of the network.

In summary, when dealing with high-dimensional inputs such as images, it is impractical to connect all neurons in a layer to all neurons in the previous volume. Instead, each neuron is connected to only a local region of the input volume. The spatial extent of this connectivity is typically called the receptive field of the neuron (equivalently this is the filter size). The extent of the connectivity along the depth axis is always equal to the depth of the input volume. The asymmetry is in how the spatial dimensions (width and height) are treated with respect to the depth dimension: The connections are local in space (along width and height), but always full along the entire depth of the input volume.

Convolutional neural networks thus are a particularly practical way to analyze camera image data to search for falls or other significant events.

SUMMARY OF THE INVENTION

The present invention relates to a system and method for activity recognition such as detecting, analyzing and preventing events such as falls and wanderings involved in the care of cognitively impaired individuals through video recording. The system includes video cameras that typically begin recording on detecting motion, a local computing unit at the care location, and a cloud or other remote computing unit. The local computing unit aggregates, stores, processes, and transmits data including performing event detection through a convolutional neural network or other artificial intelligence technique and generating appropriate alerts. The cloud computing aggregates data from many managed care communities, trains new convolutional neural networks from this data, distributes these networks to the local computing units to perform event detection, and provides a platform for various stakeholders to view and analyze the collected video data and generated alerts. The present invention thus relates to a system and method for event prevention and detection, especially falls and wanderings for the cognitively impaired via artificial intelligence applied to a realtime video stream. One embodiment uses the invention to observe dementia patients' externalization of high-risk issues, understand why they occurred and the nature of the injury received, and then uses this information to mitigate the rates of future issues as well as provide more accurate information on the nature of the injury to assist medical personnel to accurate diagnose the injury, minimize the expense of exploratory testing and optimize treatment and care.

DESCRIPTION OF THE FIGURES

Attention is now directed to several drawings that illustrate features of the present invention.

Several figures and illustrations have been provided to aid in understanding the present invention. The scope of the present invention is not limited to what is shown in the figures.

DESCRIPTION OF THE PREFERRED EMBODIMENTS

The present invention relates to a system and method for activity recognition such as detecting and preventing events involved in care for cognitively impaired persons through video recording. The system includes a plurality of video cameras, a local computing unit at a care location, and a cloud or other remote computing unit. The local computing unit aggregates, stores, processes and transmits data including performing event detection through a convolutional neural network or other artificial intelligence technique and generating appropriate alerts. The cloud or remote computing aggregates data from many managed care communities, trains new convolutional neural networks from this data, distributes these networks to the local computing units to perform event detection, and provides a platform for various stakeholder to view the collected video data and generated alerts.

The present invention applies convolutional neural networks and/or other artificial intelligence techniques to realtime video streams that typically originate from cameras set up in patient's rooms, living quarters or elsewhere. One application is to use the system to observe dementia patients' externalization of high-risk issues, understand why they occurred, and use this information to mitigate the rates of future issues.

Although there are many applications of the present invention in addressing various dementia-related issues, the invention is particularly applicable to fall detection and prevention. Therefore, the invention will be described primarily in terms of fall detection, without limiting the scope of its use in many other applications.

The method and system of the current invention differs from current vision-based care methods.

Prior art solution #1—one-to-one care
  Infeasible with larger populations; expensive
Prior art solution #2—bed alarms, wearables, non-wearables
  Works in detecting falls occur, but not how they occur
Prior art solution #3—SAR/Radar
  Invasive; costly; can't robustly handle false alarms
Prior art solution #4—Vision-based solutions
  Does not address human-reviewable screening tool for high-risk events The present invention overcomes the difficulties with these prior art techniques.

Figure 1:
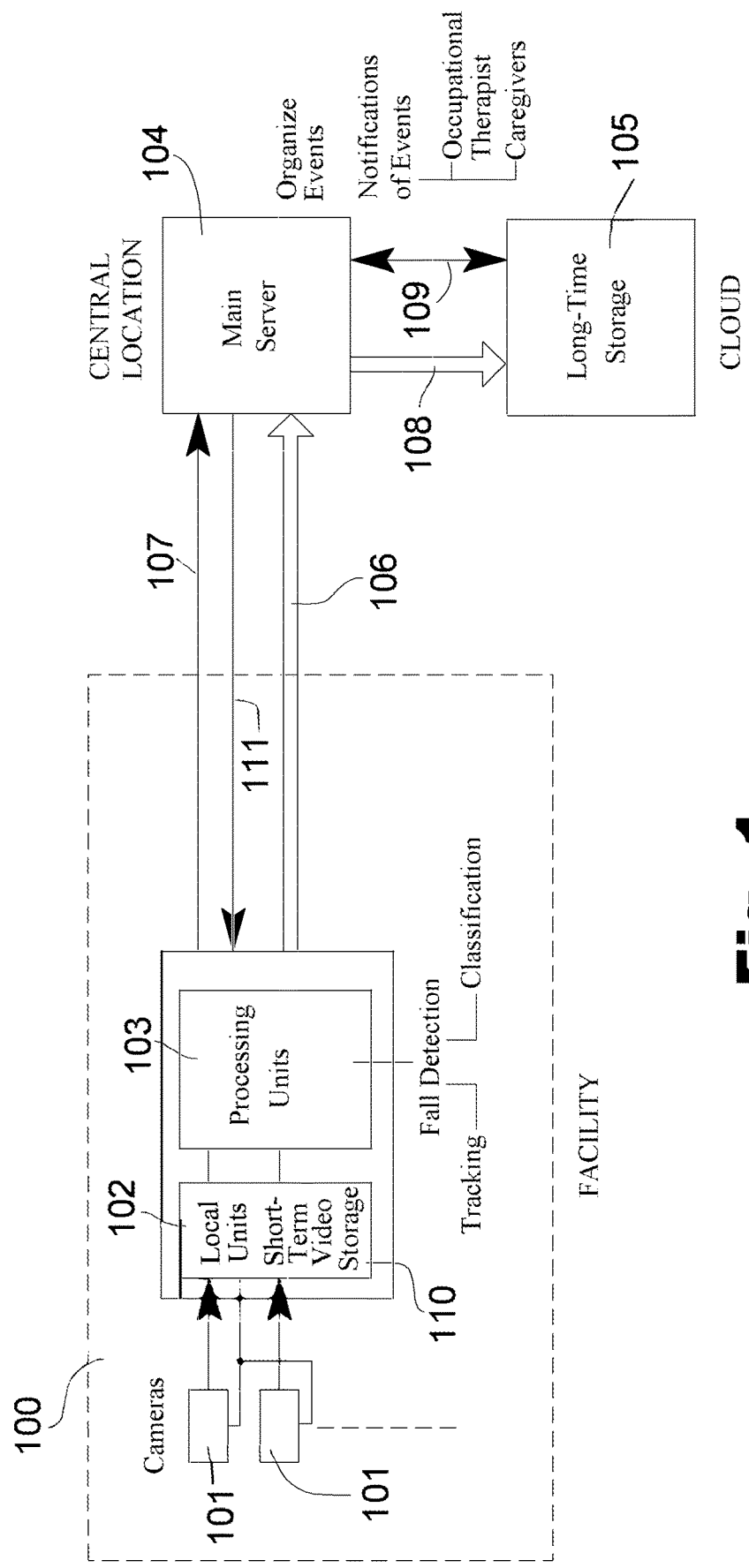
FIG. 1 is a simplified block diagram of an embodiment of the present invention.

The techniques of the present invention:
  Can be used in larger populations
  Less expensive
  Can robustly handle false alarms by enabling remote human review
  Not invasive
  Can detect that a fall occurred, and explain how it occurred by providing human-reviewable screening tools for high-risk events FIG. 1 shows a simplified block diagram of an embodiment of the present invention. The system is oriented to tracking multiple patients in a single setting. An embodiment of the system generally includes one or more cameras for capturing data of the setting; a local processing unit for storing the image data; a cloud-based data analytics server that uses object recognition to detect objects, and interpolation to track the objects' activity and occlusivity; and a database for historical data mining and analytics which synthesizes the data and transfers it back to the local processing unit.

Turning to FIG. 1, a care facility 100 can be seen. Located within the facility are a set of cameras 101. The present invention does not place any limits on how many cameras may be used providing there is sufficient processing power provided at the facility to handle all the cameras. Generally, the cameras only begin recording upon sensing motion. There is no reason to stream or store static, unchanging video. However, in order to completely capture an event, a particular camera should turn on quickly when motion occurs. Motion sensors known in the art such as infra-red sensors or ultra-sonic sensors may be used with each camera, or frame-to-frame differencing can detect motion and start the camera. Some patients who seem to be more prone to fall events may have more than one camera in their room or location. However, typically, one camera is assigned per person of interest.

Each camera 101 feeds video to, and receives control signals from, a local unit 102 that includes short-term video storage 110. The short-term storage may run from tens of seconds to several minutes depending upon the requirements of downstream processing. The preferred short-term storage is about 90 seconds. The preferred short-term storage is write-over of a fixed-length buffer or track.

The local units 102 and short-term storage 110 feed video and optional metadata to local processing units 103. These are typically fast hardware processors 103 that perform detection using a preferred method of a convolutional neural network or other artificial intelligence technique. Video of detected events is transmitted 106 via a network to a main server 104 at a remote central location. In addition, event notification is also transmitted 107 to the main server 104. Command signals 111 can be returned from the central location also via the network.

At the central location, a main server 104 is used to organize events, provide notification of events to stakeholders such as the care facility and human analysts. Alerts can be verified by a human, usually using an alert company or verified by artificial intelligence. Video sequences representing verified events are transmitted 108 and stored in long-term storage 105. This long-term storage 105 may be co-located with the main server 104, or may be remote such as a cloud storage arrangement. Organized events, along with their associated video, can then be periodically or in real time transmitted to a human verifier, to an occupational therapist or other professional(s) and to caregivers. Data mining techniques can be used to develop new training for the neural net detection or to develop new detection techniques.

Figure 2:
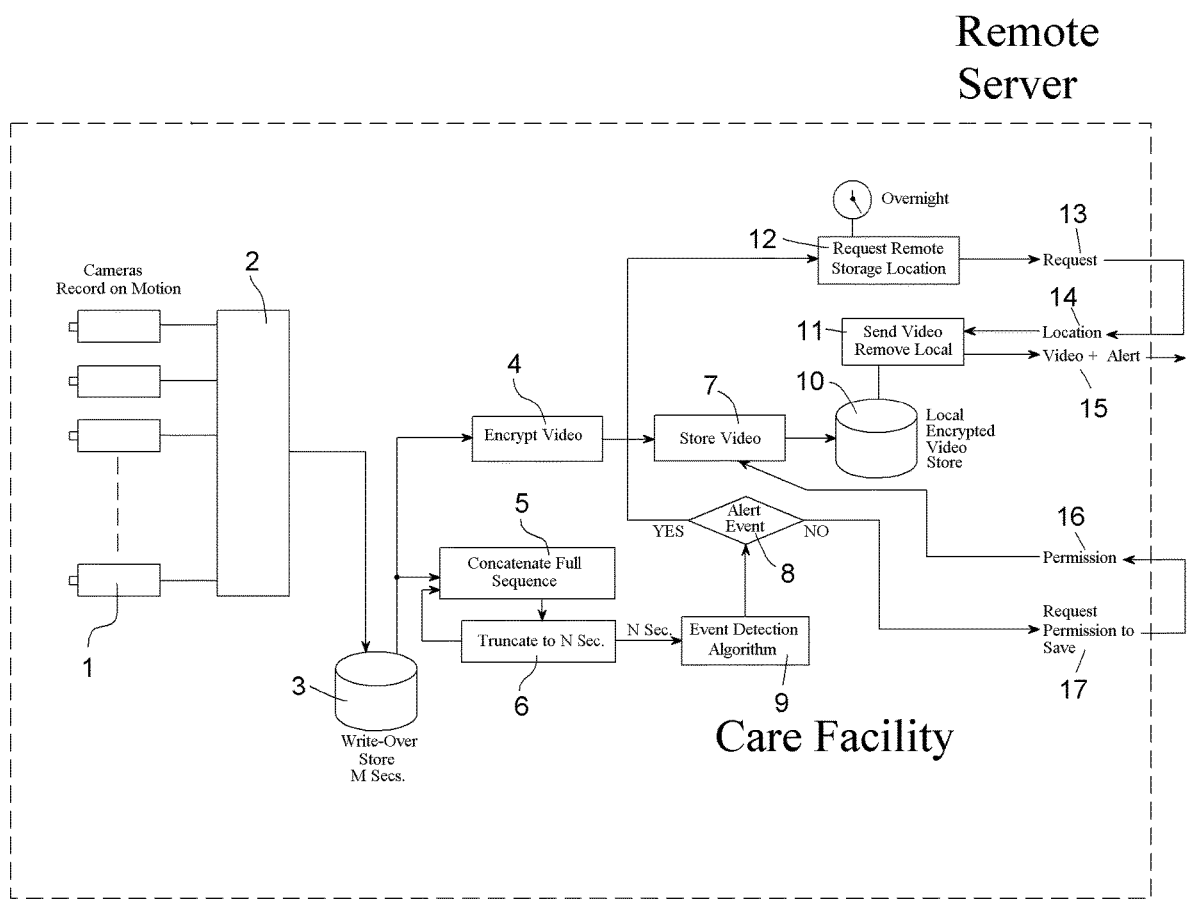
FIGS. 2-3 are parts of a detailed block diagram of the embodiment of FIG. 1.
Figure 3:
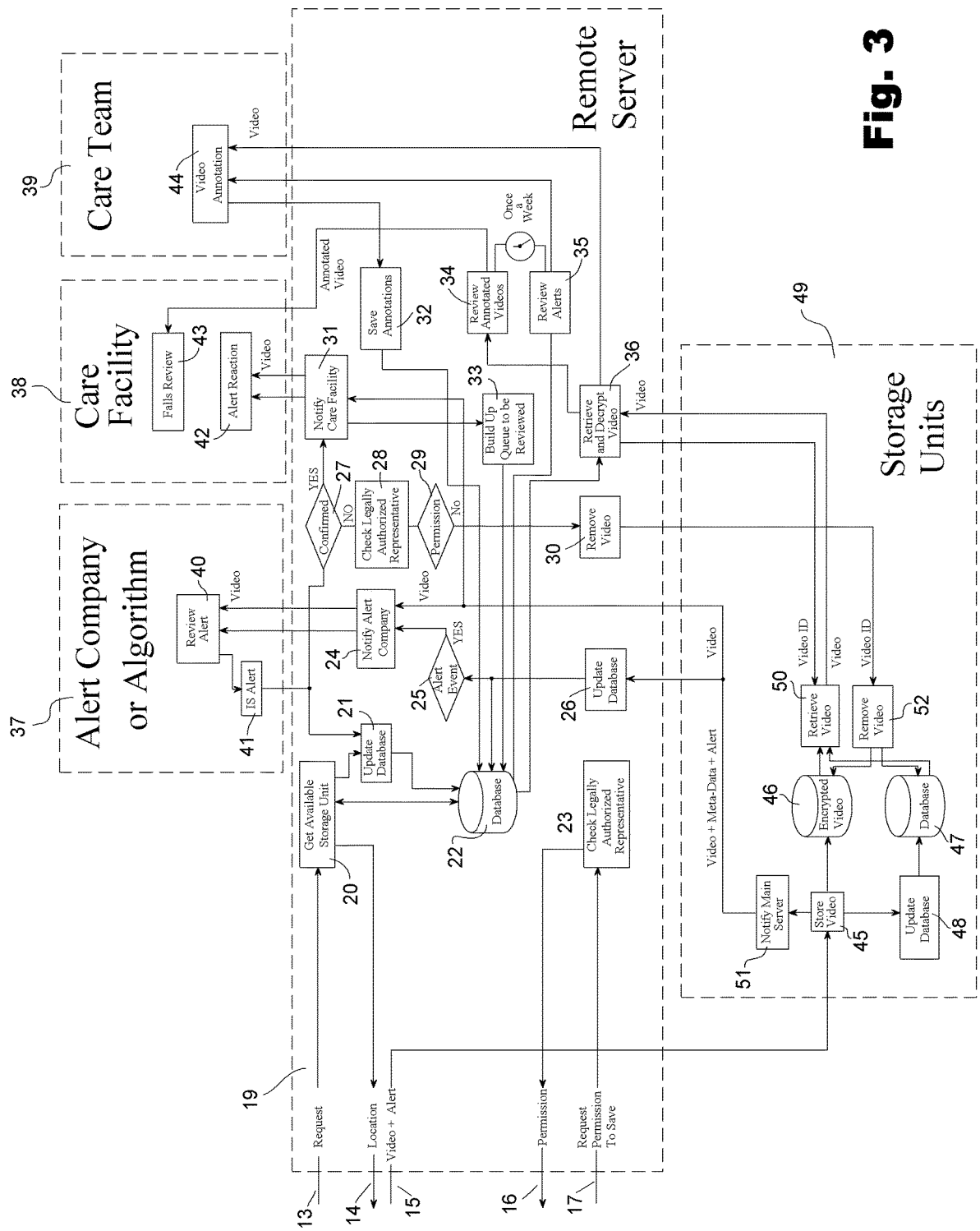

FIGS. 2-3 show an embodiment of the system of the present invention in much greater detail. FIG. 2 shows the care facility 100. Cameras 1-M 1 feed video into, and receive control signals from, a series of local units 2, where M is a positive integer. These local units channel the video onto a proper buffer or track on a short-term storage device 3. The short-term storage device can be a group of solid-state memories, a disk, or any other memory device. Short-term storage only begins recording on a particular track when the associated camera senses motion in its field of view. The short-term storage 3 of a particular track typically lasts around 90 seconds; however, this may be varied depending upon the requirements of the detection process.

Stored video from the short-term storage 3 is prepared by concatenation of the entire sequence combined with truncation to a segment to be analyzed for the processor. A segment can be approximately 60 seconds; however, the exact requirement depends upon the requirements of the detection process. A fall event usually only lasts a few seconds, so most of the video in the 60 second interval does not contain data of interest. Also, a fall event is considered a rare event which hopefully does not occur often. In this case, the entire video sequence from when a camera first detects motion until it shuts down usually does not contain an event of interest. Cameras are activated by care-takers and guest entering the field of view as well as by movement of the person of interest. A fall event (or other event of interest) is thus a needle in a haystack of video data even with camera turn-on only on motion. In order to find such events, all of the short-term video segments must be fed through the detection process. Most of the time, the output of detection is a low score (meaning there was no event of interest). However, in order to not miss events, the detection threshold must be set reasonably low. This means there will be false positive detections (declaring a fall event when there really was no fall). Final verification of an event can be performed remotely by a human who plays back the video. This may be done by an alert company or others. Verification can be performed in near real-time when the system is used to immediately report events back to the facility, or it can be done later offline for the purpose of analyzing events and generating new training for the neural network or other detection process.

The video from the concatenate/truncate operations 5, 6 enters the hardware detection processors 9 for alert detection. There can be one or several very fast processors that process several channels of video data, or there can be a dedicated hardware processor for each channel. A preferred processor is a GPU manufactured by Nvidia or the like. Video segments of N seconds are analyzed by the processor, where N is a positive integer. Each segment consists of a collection of 2-dimensional image frames. It is these frame collections that are raw data into the detection processors 9.

For each short-term segment, a decision 8 is made whether there is an event or not. In the case of motion with no event, a request 17 is sent to the remote main server (FIG. 3) for storage, and a database is queried to check on an instruction from a legally authorized representative as to whether the video sequence is to be saved or not. Video data is typically encrypted with an encryption unit 4 for privacy. If permission to store 16 is returned from the main server, the encrypted sequence is stored on an encrypted video store 10. In the case of an alert (unverified detected event), the encrypted video is stored 7 on the encrypted server 10 without requesting permission. Also, a request 12, 13 is made for remote storage. When a remote location is returned 14 from the main server, the stored video is assigned a permanent video ID and is sent 11 for remote storage and analysis. The video may be transferred immediately for realtime verification, or event video may be transmitted periodically such as overnight. For each event stored, a request for remote storage is made, and if granted, the video is transmitted and stored. Other event information including metadata about the event is typically transmitted with the alert and the sequence of video frames related to the event. This event information can include the date, time start, time stop camera number, and event score as well as any other information concerning the event.

Turning to FIG. 3, a diagram of the remote parts of the system of the present invention can be seen. FIG. 3 is a continuation to the right of FIG. 2. Incoming requests for remote storage 13 are processed by storage control 20 at the main server 19. Storage locations 14 are sent back to the facility for video transmission. Video 15 and alert data is then sent to a video storage control 45 at the remote long-term storage location 49. In addition, a master SQL (or other) database 22 is updated with all non-video data concerning the event and/or video being stored. All stored video is assigned a video identification (ID). Requests 17 for facility local storage of non-event video are received and processed by a module 23 that checks a stored instructions from a legally authorized representative or other instructions. Permissions or denials for such storage 17 are returned to the care facility.

In the case of received event video at the video storage control 45, the main server 19 is notified 51. This causes the main database 22 to be updated that video is present and stored, and if it the video represented 21 an event, a remote alert company 37 can also be notified 24, and the associated video can be sent to the alert company. The job of the alert company 37 is to review 40 the alert and determine its validity or non-validity. This can also be done with artificial intelligence. If it is determined that the event is a true alert 41, the main server 19 can be notified, and the database 22 is updated that the alert is verified. The alert company 37 typically uses a human evaluator to make the final validity determination. If event validity is determined in real-time, the alert company can also directly notify the care facility at that time, or the main server can confirm 27 the event and notify 31. The care facility 38 can then execute alert reaction 48 instructions. The alert can cause an audio or other alarm to sound at the care facility to notify personnel that they must immediately respond. In the case that the event is determined to not be an alert 27, the instructions from the legally authorized representative or other instructions can be consulted 28 and permission 29 can be granted to remove the video 30 from storage.

The cloud or other remote storage 49 stores encrypted video 46 and maintains its own local database 47 that is generally a catalog of what video is stored. Interfaces 50, 51 receive a video ID along with a command to, for example, retrieve the video or to remove the video. When a remove video command is received by interface 52, the video is erased from storage 46, and the storage database 40 is updated. When a retrieve video command is received by interface 50, the requested video is transmitted to the main server.

One of the functions of the main server 19 is to allow offline analysis of events. A queue 33 of events to be reviewed is stored in the main database 27. Periodically, this queue is used to retrieve video event segments for analysis. A particular module 36 retrieves and decrypts each video segment on the queue. The raw segments are then transmitted to an occupational therapist 39 or other reviewing professional. Usually alerts are reviewed 35 on a time schedule such as once a week, or on any other schedule. The occupational therapist, care team or other professional 38 or typically annotates 44 the alert data and video. Annotated alerts are sent back to the main server 19, and the annotations are saved 32 in the main database 22 as metadata on the alert. The alert video ID is always associated with the alert as well. Annotated alerts, along with their associated video, can also be sent periodically to the care facility 38 for review by a fall review 43 committee.

The data collected can be analyzed to facilitate changes in the given setting which can mitigate potential risk factors for the onset or continuation of various dementia-related issues. One object of the data collection is to detect fall rates, analyze their causes, and adjust the setting accordingly, lowering future fall rates. Another object is to monitor caretakers' activity to ensure they are maintaining proper preventative measures to avoid further issues. For example, an individual who is bedridden must be turned in bed every two hours, as a protective factor for the onset of pressure sores. Data collection can determine to what extent or how frequently an individual was turned. An alert can be generated if the individual has not changed position, either independently or with the help of a caregiver, within a predetermined time window.

Detection of an alert event such as a fall requires image pattern recognition. A fall, for example, may be represented by a human form prone or partially prone on the floor or on hands and knees or other unusual position. A fall is also represented by faster than normal frame to frame differences (fast motion over relatively few frames).

Figure 4:
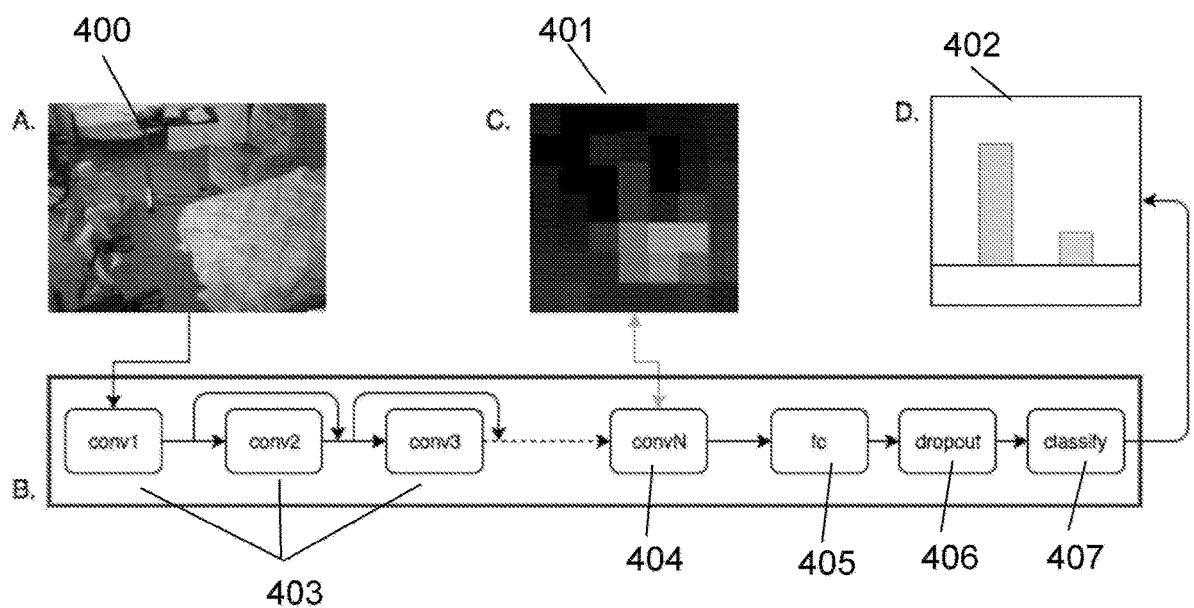
FIG. 4 shows the flow process of a convolutional neural network.

FIG. 4 shows a block diagram of an embodiment of a convolutional neural network fall event detector. In this embodiment, the processing is represented as a pipeline of N convolutional filters 403, where N is a positive integer and the last filter is marked as cony N 404. This pipeline is followed by a fully connected (fc) layer 405. This is a neural layer that connects to every neuron on the previous layer. This fully connected layer 405 produces output scores for regions of the input image. There are usually a large number of scores at this stage. A dropout layer 406 culls out only the most important scores by applying hard thresholds. Finally, a classification layer 407 makes a decision as to whether there is an event of interest (alert) embedded in the raw input image. The image data typically spans many frames of 2-dimensional input. Numerous additional techniques known in the art of image processing and neural networks my also optionally be applied to the process such as zero-padding, backward convolution, down-sampling and many others.

FIG. 4 shows a 2-dimensional image frame 400 being fed into the input of the convolutional pipeline 403. It can be seen that the image contains a bed on the right, some static furniture in the background, and what appears to be a human form on the lower left. It should be noted that the raw image 400 is a color image and thus typically has a red, green blue components (or other convenient orthogonal bases). The pipeline 403 can process the three color images separately in parallel, or can combine the processing of all colors in a single path. A block vector image (in color) 401 is shown as the result of the Nth convolutional filter layer. The fully-connected layer 404 converts this color matrix into a set of scores. For each frame, there is typically a score for each subregion of the 2-dimensional image. The entire sequence contains many such images. The dropout layer combines scores for single or multiple frames into major scores. The classifier 407 than produces the final score set 402 from which a decision as to the existence of an alert can be made. The final score is typically based on the entire sequence analyzed.

FIG. 4 shows a single 2-dimensional input frame image 400. However, as stated, the actual input from the system is around 60 seconds of streamed video that contains many frames. Hence, the time dimension is always present in the raw data. The final classification and decision as to an event is based not only on pattern recognition in single images 400, but on a time sequence of such images (frames). For example, the image 400 appears to show a prone human form in the lower left. However, the room camera started recording the sequence video based on motion. Thus, earlier frames may contain images of someone standing or getting out of bed followed by a fall which would be a rapid frame-to-frame change (large differences between successive frames). Thus the image 400 may be the last in a chain of frames that are rich in information. Thus pattern recognition and recognition of frame-to-frame changes, as well as their rapidity also play a very important role in final event classification. Other techniques such as interpolation can also be used to track motion.

The present invention relates to a method for tracking multiple people in a single setting as well as a system for doing that. In various embodiments, the method includes: capturing image data of the setting; detecting and tracking all objects in the image data; analyzing features of the objects and determining their level of occlusivity and activity; and informing a third party of the detected events and behavior. The "people of interest" are typically individuals with dementia. The term "people" refers to individuals associated with caring for or otherwise occupying the same setting as the people of interest.

Preferably, the monitoring involves focusing on all objects and understanding how they coexist to affect the people of interest. The monitoring involves analyzing a temporal sequence of events concerning the people of interest, and more specifically, tracking all of the surrounding objects and people in the image data to understand their roles in affecting the people of interest.

It should be noted that in a particular embodiment of the present invention, the entire event validation, alert and response process, as well as long-term storage of the associated video sequence can be performed entirely at the care facility. This is the case of a stand-alone system. However, such a system, even though autonomous, can also report and rely alerts, event information and video to a master facility or main server.

Several descriptions and illustrations have been presented to aid in understanding the present invention. One with skill in the art will realize that numerous changes and variations may be made without departing from the spirit of the invention. Each of these changes and variations is within the scope of the present invention.

We claim:

1. An apparatus, comprising:
a 2-dimensional camera configured to be disposed within a care location and configured to record within a field of view of the 2-dimensional camera, to generate a sequence of 2-dimensional video frames,
a memory operatively coupled to the camera and configured to store the sequence of 2-dimensional video frames,
a processor operatively coupled to the camera and configured to receive from a remote compute device a convolutional neural network (CNN) trained based on aggregate data from a plurality of care locations,
the processor configured to detect an event of interest from a set of predetermined events of interest and from the sequence of 2-dimensional video frames using the CNN, the processor configured to define an event alert upon detection of the event of interest, including event information;
the processor configured to produce a final classification and detection decision of the event of interest based on both pattern recognition and on the sequence of 2-dimensional video frames;
the processor configured to transfer the event alert, the event information and the sequence of 2-dimensional video frames relating to the event of interest over a communications network to a remote server that also receives notification of event validity for each event of interest from an event verification location upon receiving the event information and the sequence of 2-dimensional video frames.

2. The apparatus of claim 1, wherein the event alert, the event information and the sequence of 2-dimensional video frames are periodically retrieved from a remote memory and annotated by an analyst for data mining.

3. The apparatus of claim 1, further comprising:
a preprocessor operatively coupled to the processor and configured to truncate the sequence of 2-dimensional video frames to only frames relating to the event of interest for verification.

4. The apparatus of claim 1, wherein the event of interest is a fall event.

5. The apparatus of claim 1, wherein the event of interest is a wandering event.

6. The apparatus of claim 1, wherein the event of interest is a person with cognitive impairment standing without anyone else in a room the care location.

7. The apparatus of claim 1, wherein the event of interest is failure to timely attend to a stationary at-risk individual.

8. The apparatus of claim 1, wherein the event of interest is a person with cognitive impairment leaving an area without anyone else in the sequence of 2-dimensional video frames.

9. The apparatus of claim 1, wherein the event of interest is a significant reduction in gait speed of a particular individual.

10. The apparatus of claim 1, wherein:
the event of interest is an activity performed by a caregiver,
the processor configured to define the event alert upon detection of the event of interest and based on a time characteristic of the activity performed by the caregiver.

11. The apparatus of claim 1, wherein the remote server is configured to store metadata relating to events and event alerts in a remote memory.

12. The apparatus of claim 1, further comprising:
a segmentor operatively coupled to the processor and configured to segment the sequence of 2-dimensional video frames into frames representing an event of interest and frames not representing an event of interest, the frames representing an event of interest are automatically recorded on the memory, and the frames not representing an event of interest require approval to be stored on a remote memory.

13. The apparatus of claim 1, wherein the notification of event validity is received from an event validity algorithm executing on the remote server.

14. An apparatus, comprising:
a 2-dimensional camera configured to be disposed within a care location and configured to record within a field of view of the 2-dimensional camera, to generate a sequence of 2-dimensional video frames,
a memory operatively coupled to the 2-dimensional camera and configured to store a convolutional neural network (CNN) trained based on aggregate data from a plurality of care locations,
a processor operatively coupled to the 2-dimensional camera and configured to detect from the sequence of 2-dimensional video frames a characteristic of an activity that includes at least one of (1) an activity performed by a caregiver, (2) a time of the activity performed by the caregiver, (3) an activity performed by a at-risk individual, or (4) a time of the activity performed by the at-risk individual, the processor configured to create an activity alert upon detection of the characteristic of the activity, including activity information;
the processor configured to produce a final classification and a detection decision of the characteristic of the activity based on both pattern recognition and on the sequence of 2-dimensional video frames, with larger frame-to-frame pattern changes resulting in higher detection scores;
the processor configured to transfer the activity alert, the activity information and the sequence of 2-dimensional video frames relating to the characteristic of the activity over a communications network to a remote server that receives notification of validity from an analysis service upon receiving the activity information and the sequence of 2-dimensional video frames.

15. The apparatus of claim 14, wherein the remote server is configured to store the activity alert, the activity information and the sequence of 2-dimensional frames on a remote memory.

16. An apparatus, comprising:
a 2-dimensional camera configured to be disposed at a care location and configured to record in a first of view of the 2-dimensional camera, to generate a sequence of video frames,
a processor operatively coupled to the 2-dimensional camera and configured to detect a plurality of events of interest from a sequence of video frames,
the processor configured to generate an event alert upon detection of an event from the plurality of events of interest, including event information, using a convolutional neural network trained from data collected from a plurality of care locations;
the processor configured to produce a final classification and detection decision of the event based on both pattern recognition and on the sequence of video frames, with larger frame-to-frame pattern changes resulting in higher detection scores;
the processor configured to transfer the event alert, the event information and the sequence of video frames relating to the event over a communications network to a remote server that receives notification of event validity upon receiving the event information and the sequence of video frames, and that analyzes the sequence of video frames to identify an impact of the plurality of events of interest on staff and at-risk individual safety.

17. The apparatus of claim 16, wherein the event alert, the event information and the sequence of video frames are periodically retrieved and annotated by an analyst.

18. The apparatus of claim 16, wherein the sequence of video frames is encrypted.

19. The apparatus of claim 16, wherein the event of interest is a fall event.

20. The apparatus of claim 16, wherein the event of interest is a wandering event.

21. The apparatus of claim 16, wherein:
the event of interest is an activity performed by a caregiver,
the processor configured to define the event alert upon detection of the event of interest and based on a time characteristic of the activity performed by the caregiver.

22. The apparatus of claim 16, wherein the remote server is configured to provide marketing resources for a care facility to demonstrate quality of care provided.

* * * * *